(12) United States Patent
Arora et al.

(10) Patent No.: US 7,579,514 B2
(45) Date of Patent: Aug. 25, 2009

(54) ABSORBENT ARTICLES HAVING FLOCKED FIBERS

(75) Inventors: Tarun K. Arora, Edison, NJ (US); Vincent P. Lasko, New Egypt, NJ (US); H. Michael Moscherosch, Doylestown, PA (US)

(73) Assignee: McNeil-PPC, Inc., Skillman, NJ (US)

( * ) Notice: Subject to any disclaimer, the term of this patent is extended or adjusted under 35 U.S.C. 154(b) by 861 days.

(21) Appl. No.: 10/281,810

(22) Filed: Oct. 28, 2002

(65) Prior Publication Data
US 2004/0082929 A1    Apr. 29, 2004

(51) Int. Cl.
*A61F 13/15* (2006.01)
*A61F 13/20* (2006.01)

(52) U.S. Cl. .................. 604/365; 604/384; 604/385.01

(58) Field of Classification Search ......... 604/364–365, 604/367, 387, 354, 385.03, 385.23, 385.01, 604/384, 378
See application file for complete search history.

(56) References Cited

U.S. PATENT DOCUMENTS

| | | |
|---|---|---|
| 2,527,501 A | 10/1950 | Saks |
| 2,691,611 A | 10/1954 | Saks |
| 3,436,442 A | 4/1969 | Saks |
| 3,672,929 A | 6/1972 | Riordan |
| 4,917,697 A | 4/1990 | Osborn, III et al. |
| 5,474,818 A | 12/1995 | Ulrich et al. |
| 2001/0008672 A1* | 7/2001 | Norvell et al. ............ 428/90 |
| 2003/0216704 A1* | 11/2003 | George ............... 604/364 |

FOREIGN PATENT DOCUMENTS

| | | |
|---|---|---|
| EP | 0737462 B1 | 9/2000 |
| EP | 1 136 050 A1 | 9/2001 |
| EP | 1147756 A2 | 10/2001 |

OTHER PUBLICATIONS

American Flock Association; "Design With Flock in Mind" Brochure; American Flock Asssociation, 230 Congress Stree, Boston, MA 02110; phone (617) 524-8220; fax (617) 542-2199.
European Search Report dated Dec. 19, 2003, for corresponding EP 03024573.2.

* cited by examiner

*Primary Examiner*—Michele Kidwell

(57) ABSTRACT

The present invention relates to an absorbent article having a body-facing surface and a garment-facing surface opposite the body-facing surface, wherein the garment-facing surface has a substantially tack-free adhesive coating and sticky fibers flocked thereon for securing the absorbent article in place.

14 Claims, 1 Drawing Sheet

ABSORBENT ARTICLES HAVING FLOCKED FIBERS

FIELD OF THE INVENTION

The present invention relates to an absorbent article, such as a sanitary napkin, pantiliner, shoe insert, incontinence pad, garment pad, breast pad and the like, using flocked fibers to secure the absorbent article in place.

BACKGROUND OF THE INVENTION

Absorbent articles, such as sanitary napkins, pantiliners, breast pads, and incontinence pads are secured to a user's garment during use. Such attachment is typically accomplished using an adhesive that has been coated on the garment-facing surface of the absorbent article. Such adhesive is typically tacky upon curing. Due to the tacky properties of such adhesive, the adhesive coating is prone to adhering dirt, dust and the like before the adhesive article is place in its desired location. Such adhesion reduces the surface area of the adhesive coating available for securing the absorbent article in place, which reduces the stay-in-place properties of the absorbent article having adhesive coating on the garment-facing surface.

Several solutions have been proposed to overcome such problems with adhesive coatings that are tacky to the touch. One common solution is to provide a separate release strip, e.g., release paper, that covers the adhesive coating prior to securing the absorbent article to the garment. The release strip acts as a protective barrier for the adhesive coating during manufacture, package, and storage of the absorbent article.

The release strip typically used in the art is a silicone-coated material, e.g., paper, which permits easy removal of the release strip from the garment facing side of the product due to the nonstick characteristic of silicone. Examples of a release paper are described in U.S. Pat. No. 4,917,697.

These proposed solutions suffer from several drawbacks for both the user of the absorbent article and the manufacturer of the absorbent article. For the user, the release strip must be removed just prior to application of the product. Such a process can be clumsy, untimely, and is a source of possible embarrassment in certain situations. For the manufacture, the inclusion of release paper adds cost and time for the manufacture of such absorbent articles. Additionally, noise is generated upon the removal and disposal of release paper.

U.S. Pat. No. 5,474,818 discloses the elimination of release paper as another attempted solution. This document discloses a method for the formation of flexible containers such as pouches, bags, or envelopes which have an interior surface coated with a composition which has nonstick characteristics and which lacks the thermoplastic characteristics of conventional heat sealing for forming seams by heat sealing. The document also discloses that the pouch is formed from a silicone polymer coated paper with the silicone coating forming an internal surface of the pouch, thereby allowing easy removal of the product from the pouch and avoiding permanent sticking of the pressure sensitive adhesive coating to the pouch material.

This proposed solution also suffers from several drawbacks. The absorbent article must be packaged in a flexible container. This creates a disposal problem for the user and increases costs for the manufacturer.

EP 1 147 756 discloses another solution that uses a substantially tack-free, high-coefficient of friction backsheet having at least one tape tab affixed to its outwardly disposed surface. Such design overcomes the problem of shifting and separation from an undergarment when the user urinates or initiates usage of the article for the first time. However, this solution is economically disadvantageous for the manufacturer.

It is known that EP 0 737 462 A1 discloses a sheet material for use in absorbent articles, whose visual and tactile properties are closer to those of a piece of fabric, whilst allegedly retaining all the typical advantages of plastic film. Such film is described as being used to cover the outside of an absorbent product, wherein at least part of the surface outside of the absorbent product contains a layer of fibers applied by flocking in order to give the absorbent product improved tactile properties over products that employ plastic films against the skin.

Flocking is a technique primarily used in the fabric industry by which fibers are fixed in a vertical position on a substrate. Recently, however, flocking has been described in conjunction with absorbent articles. For example, EP 0 737 462 A1 discloses the use of a sheet material to cover the outside of an absorbent product, wherein at least one portion of sheet material bears a layer of fibers applied by flocking, "i.e. anchored to the surface of the sheet material by a layer of resin or other adhesive and aligned substantially at right angles to the surfaces of the [ ]laminated material to cover the outside of an absorbent product, wherein at least one portion of the surface of the laminated material bears a layer of fibers applied by flocking." According to this document, the flocked fibers are located on the external surface of the absorbent product in order to give the absorbent product improved tactile properties over products that employ plastic films against the skin. However, due to flocking fibers at substantially right angles to the surface of the substrate, articles having such flocked fibers on the garment facing side do not have sufficient adhering properties to maintain an absorbent article in place during use.

What is needed, therefore, is a system for securing the absorbent article to a garment that overcomes the above problems. The instant invention accomplishes this goal in a user-friendly and economical way. It is has surprisingly been discovered that a garment facing surface of an absorbent article essentially having a substantially tack-free adhesive and flocked fibers adhered thereon provides such a solution.

Additionally, absorbent articles having a flocked garment-facing surface may be stacked upon each other, forming a multiple layered absorbent article.

SUMMARY OF THE INVENTION

One embodiment of the present invention is directed to an absorbent article having a body-facing surface and a garment-facing surface opposite the body-facing surface, wherein the garment-facing surface has a substantially tack-free adhesive coating and sticky fibers flocked thereon for securing the absorbent article in place. The sticky fibers are hydrophilic fibers, hydrophobic fibers or mixtures thereof. The absorbent article can include a cover, a backsheet and an absorbent core deposed between the cover and backsheet. These sticky fibers can be flocked onto the garment facing surface by a method selected from the group consisting of electrostatic methods, mechanical methods, or a combination thereof. Additionally, the sticky fibers shape can be linear, curled, bent or mixtures thereof.

In another embodiment of the present invention, the absorbent article includes at least two layers, each layer having a cover and backsheet having a garment-facing surface, wherein each garment-facing surface has a substantially tack-free adhesive coating and sticky fibers flocked thereon for securing the absorbent article in place and wherein the first layer is releasably attached to the second layer such that the sticky fibers of said first layer are interlaced with the cover of the second layer. The sticky fibers are hydrophilic fibers, hydrophobic fibers or mixtures thereof. The absorbent article can include a cover, a backsheet and an absorbent core deposed between the cover and backsheet. The sticky fibers can be flocked onto the garment facing surface by a method selected from the group consisting of electrostatic methods, mechanical methods, or a combination thereof. Additionally, the sticky fibers shape can be linear, curled, bent or mixtures thereof.

In yet another embodiment of the present invention, the absorbent article for use with an undergarment includes a cover; and a backsheet having a garment facing surface, wherein the garment-facing surface comprises sticky fibers flocked thereon. The sticky fibers are hydrophilic fibers, hydrophobic fibers or mixtures thereof. The absorbent article can include a cover, a backsheet and an absorbent core deposed between the cover and backsheet. The sticky fibers can be flocked onto the garment facing surface by a method selected from the group consisting of electrostatic methods, mechanical methods, or a combination thereof. Additionally, the sticky fibers shape can be linear, curled, bent or mixtures thereof.

DETAILED DESCRIPTION OF THE INVENTION

This invention relates to those absorbent articles that are normally adhered to a substrate such as cloth, skin, itself, shoe insoles, breast pads, and the like. The absorbent article may for example be a sanitary napkin, a pantiliner, a diaper, incontinence pad, or other similar product for absorbing exudates from the body, such as menses, urine, breast milk, perspiration, and feces. In particular, this invention relates to a sanitary protection article such as a sanitary napkin or pantiliner that attaches to a garment. As such, in this application, the terms "absorbent article," "pantiliner," "sanitary protection article," and "sanitary napkin" are used interchangeably. Such pantiliner may have an approximately rectangular, oval, dogbone, peanut shape, or generally triangular shape, such as those used with thong-type garments. Depending on the nature of the absorbent article, its size and thickness may vary. For example, sanitary napkins typically have a caliper of about 1.4 to about 5 mm, a length of about 3 to about 16 inches, and a width of about 1 to about 5 inches. Pantiliners typically have a caliper of less than about 0.2 inches, a length of less than about 8 inches, and a width of less than about 3 inches.

The term "substantially tack-free" as used herein means yielding a value of less than 100 grams when tested on an inverted probe tester such as the Probe Tack Tester, model number 80-02, available from Testing Machines Incorporated of Mineola, Long Island, N.Y., in conjunction with the standard test method ASTM D-2979-95.

The term "sticky fibers" as used herein means fibers that have been produced such that the fiber ends, sides, or both are not clean, e.g., not smooth, and fibers that are flocked at an angle other than 90° to aid in securing the article to a substrate. For those fibers that do not have clean ends, the fiber ends may be jagged or curled or have multiple projections extending therefrom. For example, such fiber ends and sides may resemble a pine tree. Such ends may provide additional surface area for the flocked fibers to secure the absorbent article in place.

Figure 1:
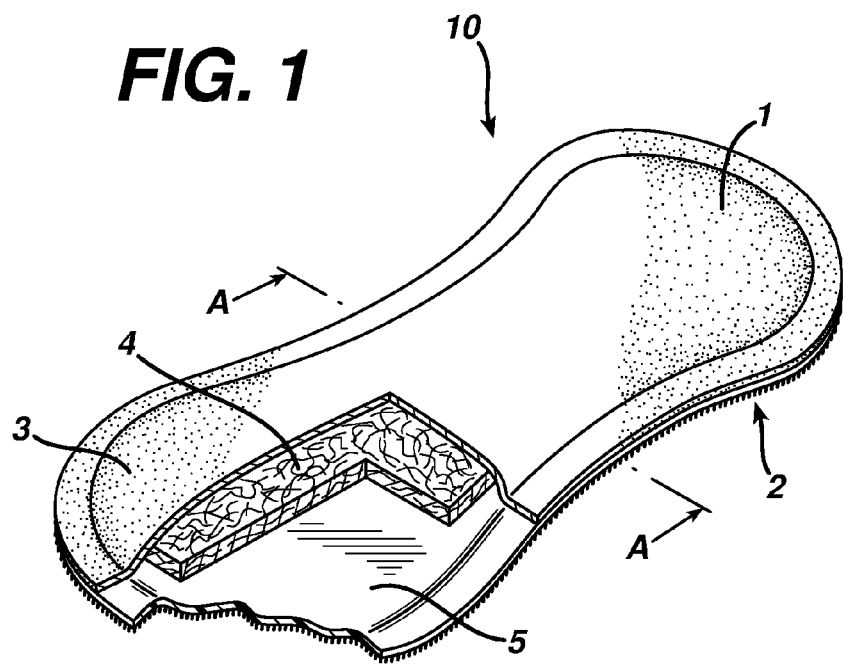
FIG. 1 is a perspective view of a pantiliner.
Figure 2:
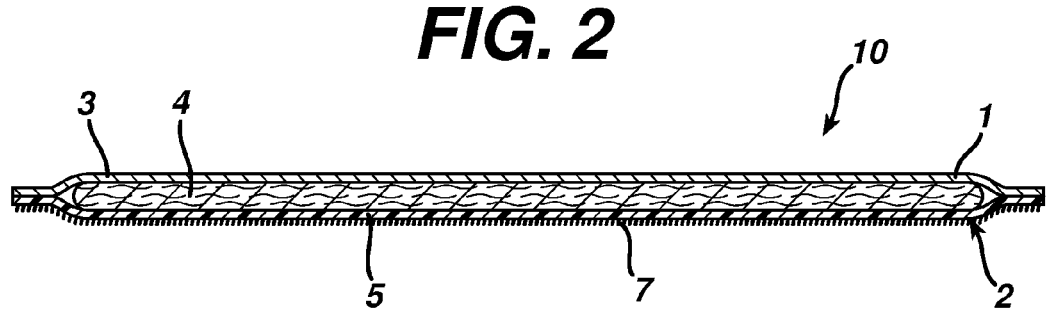
FIG. 2 is a sectional view of FIG. 1 along lines AA.

FIG. 1 depicts such a pantiliner according to the invention, and is used for purposes of illustration in the following description. The pantiliner shown in FIGS. 1 and 2 has in sequence from its body-facing surface 1 to its garment-facing surface 2, liquid permeable cover 3, an absorbent core 4, a liquid impermeable backsheet 5, and a layer of flocked fibers 7. The cover 3 of the absorbent article may be formed from any fluid pervious material that is comfortable against the skin and permits fluid to penetrate to the absorbent core, which retains the fluid. The cover should retain little or no fluid to provide a relatively dry surface, since its external surface forms the body-facing surface 1 of the article. A variety of materials are known for preparing covers, and any of these may be used. For instance, the cover may be a fibrous non-woven fabric made of fibers or filaments of polymers such as polyethylene, polypropylene, polyester, or cellulose. Alternatively, the cover may be formed from an apertured polymeric film. The thickness of the cover may vary from approximately 0.001 to 0.062 inch, depending on the material chosen.

Generally, cover 3 is a single sheet of material having a width sufficient to form the body-facing surface 1 of the article. The cover may be the same length, or optionally longer than the absorbent core so as to form transverse ends. Such transverse ends may be sealed with other layers to fully enclose the absorbent core.

As shown in FIG. 1, the pantiliner contains an absorbent core. The absorbent core 4 may be comprised of a loosely associated absorbent hydrophilic material such as cellulose fibers, including wood pulp, regenerated cellulose fibers or cotton fibers, or other absorbent materials generally known in the art, including acrylic fibers, polyvinyl alcohol fibers, peat moss and superabsorbent polymers. Optionally, the pantiliner may just have a cover and backsheet.

The absorbent article further has a liquid impermeable backsheet 5, the exterior of which forms the garment-facing surface 2 of the article. The backsheet may be any thin, flexible, body fluid impermeable material such as a polymeric film, for example, polyethylene, polypropylene, or cellophane. Alternatively, the backsheet may be a normally fluid permeable material that has been treated to be impermeable, such as impregnated fluid repellent paper or non-woven fabric material, or a flexible foam, such as polyurethane or cross-linked polyethylene. The thickness of the backsheet when formed from a polymeric film typically is about 0.0003 to 0.002 inch. A variety of materials are known in the art for use as backsheet, and any of these may be used.

Generally, the backsheet 5 is a single sheet of material having a width sufficient to form the garment-facing surface 2 of the absorbent article. The backsheet may extend around the sides of the absorbent core in a C-shaped configuration with the portions of the backsheet adjacent its longitudinal edges extending upwardly from the garment-facing surface toward the body-facing surface of the article. Preferably the backsheet is breathable, i.e., a film that is a barrier to liquids but permits gases to transpire. Materials for this purpose include polyurethane films and microporous films in which microporosity may be created by ionizing radiation or by leaching out of soluble inclusions using aqueous or nonaqueous solvents. Single or multiple layers of permeable films, fabrics, and combinations thereof that provide a tortuous path, and/or whose surface characteristics provide a liquid surface repellent to the penetration of liquids may also be used to provide a breathable backsheet.

It has now been discovered that flocked fibers may advantageously be applied to the garment-facing surfaces of an absorbent article. In an absorbent article having a cover and a backsheet, for example, the flocked fibers may be applied to the external or garment-facing surface of the backsheet. Without wishing to be bound by theory, it is believed that the fibers that are flocked on the garment facing surface of the present invention become entangled with the surface of the substrate, e.g., crotch portion of underwear, swimming suit, leotard, pantyhose, shoe insole, and the like, to which the absorbent article is pressed against, thereby securing the absorbent article in place. It is believed that entanglement can be generated via two mechanisms or a combination thereof.

One mechanism uses non-parallel fibers to essentially create entanglement with the surface of the substrate due to the angle between fibers is larger than 0 degree. This can be achieved by flocking linear fibers in a non-parallel manner or by using non-linear fibers.

Another mechanism is the use of sticky fibers that have been produced such that the fiber ends are not clean, e.g., smoothly cut perpendicular to the fiber, create entanglement with the surface of the substrate due to the ends of the fibers penetrating the surface of the substrate to exhibit resistance when removed. This effect can be achieved by any method that renders short fibers with non-clean ends such as but not limited to cutting, chopping, crushing, etc., or by using fibers that are designed to create non-clean ends such as but not limited to bicomponent fibers that are designed to split or fray at the ends.

According to the invention, pantiliner 10 has fibers 7 flocked on the garment-facing surface 2 of backsheet 5. The fibers used for flocking may be hydrophilic, hydrophobic, or a combination of the two. Examples of such fibers include hydrophilic fibers that have been treated with agents to become hydrophobic fibers, bicomponent fibers, polypropylene fibers, and polyester fibers that have been treated for example with surfactants. Polyester fibers, such as DuPont-Akra Polyester Type 11A Bright, are commercially available from DuPont Company. The fibers may also include hydrophilic fibers including absorbent fibers such as rayon fibers, acrylic fibers, nylon fibers, polyvinyl alcohol fibers, superabsorbent fibers and fibers of natural or regenerated cellulosics. In one embodiment, a type of absorbent fiber is rayon fibers.

Fibers that are hydrophobic fibers include certain olefin fibers and large denier polyester fibers, preferably having a denier of at least 3, more preferably at least 6. In one embodiment, a hydrophobic fiber is a 15 denier polyester commercially available from DuPont Company.

In one embodiment of the invention, the fibers may be made from one or more type of superabsorbent polymer fibers, a combination of superabsorbent polymer fibers and other hydrophilic fibers or a combination of superabsorbent polymer fibers, other hydrophilic fibers, and hydrophobic fibers.

Fibers used for flocking may be treated with a surfactant, such as Tween 20, commercially available from ICI Americas Inc.

The fibers may be adhered to all or a portion of the garment-facing surface of the backsheet. In an embodiment shown in FIG. 2, fibers 7 are adhered to the garment-facing surface 2 of backsheet 5.

Methods of flocking fibers onto a surface are known in the art of fabric manufacture. See for example, U.S. Pat. Nos. 2,527,501; 2,691,611; 3,436,442; and 3,672,929. Typically, a substrate is coated with adhesive on all or a portion of its surface. The coated substrate is then passed through a fiber metering station in which an electrostatic field is maintained around the substrate, using for example electrodes situated above and below the substrate. The fibers are applied to the adhesive on the substrate in the presence of the electrostatic field, which orients the fibers in a desired angle to the substrate as they contact the adhesive. The substrate is then heated, polymerizing the adhesive and anchoring the fibers. Unattached fibers may be vacuumed away.

Mechanical flocking may also be used to attach fibers to a substrate. This method usually coats a surface with fibers and is done by the beater-bar method. An adhesive-coated substrate is passed over a series of polygonal rollers that rapidly vibrate the substrate. This vibration drives the fiber into the adhesive. The fibers are delivered by a flock module for flat surfaces or by an airstream pump for three-dimensional objects. Excess fibers or unattached can be removed by vacuum.

The adhesive employed to attach the fibers to the garment facing surface is a polymerizable resin, such as modified acrylic water based compounds, for example FLEXBOND 974, 977, 983, and 986 commercially available from Air Products, CARBOTAC Adhesives (PSAs) commercially available from BF Goodrich, and CARBOBOND Adhesives (non-PSAs) also commercially available from BF Goodrich. The adhesive used is substantially-tack free. In one embodiment of the present invention, the entire garment facing surface is coated with the substantially tack-free adhesive. In another embodiment, the substantially tack-free adhesive is coated in a discontinuous pattern, e.g., dots, squares, triangles, etc. In yet another embodiment, the substantially tack free adhesive is coated in a continuous pattern, e.g., curve lines, straight lines, and the like.

Regardless of type, the length of the fiber used for flocking can be varied as appropriate. For example, if the undergarment is a specific material, a short or long length may be preferred. Additionally, the fibers may be linear or shaped. For example, the fibers may be curled, crimped, or bent. Advantageously the fibers used for flocking may be made by chopping or cutting a length of filament to a desired length. During the chopping or cutting, the fiber ends produced may advantageously be not clean, e.g., not smooth. Rather the fiber ends, sides, or both may be jagged or have multiple projections extending therefrom. For example, such fiber ends or sides may resemble a pine tree. Such fibers may provide additional surface area for the flocked fibers to secure the absorbent article in place.

The absorbent article of the present invention may include other known materials, layers, and additives, such as transfer layers, foam layers, net-like layers, odor control agents, perfumes, medicaments, moisturizers, pigments, and the like, many examples of which are known in the art. The absorbent article can optionally be embossed with decorative designs using conventional techniques.

In an additional embodiment of the present invention there is provided at least two layers. Each layer including a cover and backsheet, wherein the backsheet has a garment-facing surface and each garment-facing surface has sticky fibers flocked thereon for securing the absorbent article in place. The first layer is releasably attached to the second layer such that the sticky fibers of said first layer are interlaced with the cover of the second layer, the second layer is releasably attached to the third layer such that the sticky fibers of said second layer are interlaced with the cover of the third layer, and so on until all layers are secured to one another.

EXAMPLES

Example 1

An absorbent article having a cover and backsheet was prepared as follows:

A fiber blend of 100% polyester having a denier of 20 and a length of 1 mm or less was metered onto a fluid impermeable substrate made of 1.0 mil polyethylene film and having a coating of Air Products' FLEXBOND 974 polymerizable resin. The sticky fibers, having nonclean ends were oriented in the vertical position via an electrostatic field. The fibers adhered where the resin was applied. The substrate was then passed through an oven to polymerize the resin, anchoring the fibers to the polyethylene film. The excess fibers were vacuumed away. A fluid permeable, nonwoven cover was placed onto the unflocked surface of the substrate and crimped into place. The absorbent article was placed on the crotch portion of an undergarment.

Example 2

Multiple pantiliners were made according to the method of Example 1. When a first pantiliner was laid on top of a second pantiliner, the flocked surface adhered to the cover of the second. This resulted in a layered pantiliner.

The specification and embodiments above are presented to aid in the complete and non-limiting understanding of the invention disclosed herein. Since many variations and embodiments of the invention can be made without departing from the spirit and scope, the invention resides in the claims hereafter appended.

What is claimed is:

1. An absorbent article comprising:
  a. a body-facing surface, and
  b. a garment-facing surface opposite the body-facing surface, wherein the garment-facing surface comprises a substantially tack-free adhesive coating and sticky fibers flocked thereon for securing the absorbent article to a garment.

2. An absorbent article of claim 1, wherein the sticky fibers are hydrophilic fibers, hydrophobic fibers or mixtures thereof.

3. An absorbent article of claim 1, further comprising a cover and a backsheet.

4. An absorbent article of claim 3, further comprising an absorbent core between the cover and backsheet.

5. An absorbent article of claim 1, wherein the sticky fibers are flocked onto the garment facing surface by a method selected from the group consisting of electrostatic methods, mechanical methods, or a combination thereof.

6. An absorbent article of claim 2, wherein the sticky fibers are flocked onto the garment facing surface by a method selected from the group consisting of electrostatic methods, mechanical methods, or a combination thereof.

7. An absorbent article of claim 3, wherein the sticky fibers are flocked onto the garment facing surface by a method selected from the group consisting of electrostatic methods, mechanical methods, or a combination thereof.

8. An absorbent article of claim 1, wherein the sticky fibers shape is selected from the group consisting of linear, curled, bent or mixtures thereof.

9. An absorbent article of claim 2, wherein the sticky fibers shape is selected from the group consisting of linear, curled, bent or mixtures thereof.

10. An absorbent article of claim 3, wherein the sticky fibers shape is selected from the group consisting of linear, curled, bent or mixtures thereof.

11. An absorbent article for use with an undergarment, said absorbent article comprising:
  a. a cover; and
  b. a backsheet having a garment facing surface,
wherein the garment-facing surface comprises sticky fibers flocked thereon for securing said article to a garment.

12. An absorbent article according to claim 1, wherein each of the sticky fibers include an end that is curled.

13. An absorbent article according to claim 1, wherein each of the sticky fibers include an end that is jagged.

14. An absorbent article according to claim 1, wherein each of the sticky fibers include an end having multiple projections extending therefrom.

* * * * *